United States Patent [19]
Jacobs et al.

[11] Patent Number: 5,354,199
[45] Date of Patent: Oct. 11, 1994

[54] ADHESIVE FOR PACKAGED ORTHODONTIC APPLIANCE

[75] Inventors: Dwight W. Jacobs, River Falls, Wis.; Sumita B. Mitra, West St. Paul, Minn.

[73] Assignee: Minnesota Mining and Manufacturing Company, St. Paul, Minn.

[21] Appl. No.: 902,444

[22] Filed: Jun. 19, 1992

Related U.S. Application Data

[63] Continuation of Ser. No. 739,816, Aug. 2, 1991, abandoned.

[51] Int. Cl.$^5$ .............................. A61C 3/00
[52] U.S. Cl. ............................ 433/9; 106/35
[58] Field of Search ............ 433/228.1, 9; 106/35

[56] References Cited

U.S. PATENT DOCUMENTS

| | | | |
|---|---|---|---|
| 3,250,003 | 5/1966 | Collito | 32/14 |
| 4,204,325 | 5/1980 | Kaelble | 433/9 |
| 4,340,529 | 7/1982 | Lee, Jr. et al. | 524/105 |
| 4,479,782 | 10/1984 | Orlowski et al. | 433/220 |
| 4,525,256 | 6/1985 | Martin | 204/159.18 |
| 4,695,251 | 9/1987 | Randklev | 433/8 |
| 4,749,352 | 6/1988 | Nicholson | 433/9 |
| 4,948,367 | 8/1990 | Haas | 433/9 |
| 4,952,204 | 8/1990 | Korteweg | 604/1 |
| 4,954,080 | 9/1990 | Kelly et al. | 433/8 |
| 4,978,007 | 12/1990 | Jacobs et al. | 206/469 |
| 5,015,180 | 5/1991 | Randklev | 433/9 |
| 5,034,433 | 7/1991 | Cohen et al. | 523/400 |
| 5,102,332 | 4/1992 | Uthoff | 433/215 |
| 5,183,403 | 2/1993 | Masuhara et al. | 433/9 |
| 5,221,202 | 6/1993 | James | 433/9 |

FOREIGN PATENT DOCUMENTS

| | | |
|---|---|---|
| PCT/JP89/01109 | 5/1991 | PCT Int'l Appl. . |
| PCT/US92/05470 | 10/1992 | PCT Int'l Appl. . |
| 2006792A | 5/1979 | United Kingdom . |

*Primary Examiner*—Gene Mancene
*Assistant Examiner*—Nicholas B. Lucchesi
*Attorney, Agent, or Firm*—Gary L. Griswold; Walter N. Kirn; James D. Christoff

[57] ABSTRACT

A polymerizable, storage-stable adhesive for adhesive precoated orthodontic appliances includes sufficient EBDA to impart to the adhesive a viscosity that will retain an orthodontic bracket in place on a vertical tooth surface during polymerization of the adhesive.

18 Claims, 3 Drawing Sheets

ADHESIVE FOR PACKAGED ORTHODONTIC APPLIANCE

This is a continuation of application Ser. No. 07/739,816 filed Aug. 2, 1991, now abandoned.

BACKGROUND OF THE INVENTION

1. Field of the Invention

This invention relates to an orthodontic adhesive especially useful for a packaged, adhesive precoated orthodontic appliance.

2. Description of the Related Art

Orthodontic treatment concerns movement of malpositioned teeth to orthodontically correct positions. During treatment, tiny brackets are often connected to the patient's teeth, and an archwire is then secured in a slot of the brackets. The brackets are urged along the archwire by bends or twists in the archwire or by elastic members or other means in order to shift the associated teeth to desired positions.

Previously, orthodontic brackets were connected to teeth by welding or brazing each bracket to a band which was then placed over a tooth in encircling relation. In more recent years, orthodontic brackets have been directly bonded to the tooth surface, resulting in a more aesthetic appearance. Light curable adhesives have been developed which allow the orthodontist to precisely position the bracket on the tooth and then activate a lamp to cure the adhesive and securely fix the bracket in place.

Recent advances in the field of direct bonded dental articles are described in U.S. Pat. Nos. 5,015,180 and 4,978,007, both of which are assigned to the assignee of the present invention. U.S. Pat. No. 5,015,180 describes in one embodiment an orthodontic bracket and a light curable paste sandwiched between a base of the bracket and a flexible, releasably adhering cover sheet. To bond the bracket to a tooth, the cover sheet is removed from the paste and the bracket base is then applied to the tooth. Such construction represents a time savings for the orthodontist, because the orthodontist need not dispense and apply the adhesive paste to the bracket base before bonding the bracket to the tooth.

U.S. Pat. No. 4,978,007 describes in one embodiment a substrate having a recess, an orthodontic bracket having an adhesive on an exterior surface, and a release coating sandwiched between the adhesive and an interior surface of the recess. Such construction is advantageous in that the adhesive is protected in the recess from light, oxygen, water vapor and contaminants. Also, the bracket may be retained in the recess in an upright manner that facilitates grasping of the sides of the bracket by a placement instrument or other tool in order to pull the bracket and adhesive away from the release coating.

Many orthodontists prefer to use certain adhesives that are less viscous (i.e., more fluid) than other adhesives. However, some adhesives with a relatively low viscosity have been found to occasionally distort in shape or remain on the release coating described in U.S. Pat. No. 4,978,007 as the bracket is lifted from the substrate, such that the orthodontist may need to pause to re-shape the adhesive or apply additional adhesive to the bracket base.

Certain orthodontic adhesives having relatively high initial viscosities may release in a satisfactory manner from a release coating when newly mixed. However, brackets that are packaged with a pre-applied coating of adhesive may not be bonded to a patient's teeth for some time. Many conventional adhesives have relatively low molecular weight components that tend to volatilize over a period of time to such a degree that the adhesive becomes too stiff, in general, for satisfactory use for precoated brackets. On the other hand, an adhesive made with relatively high molecular weight components may have a low volatility but may be too stiff to provide sufficient adhesive strength after polymerization.

SUMMARY OF THE INVENTION

The present invention concerns an orthodontic adhesive wherein the improvement comprises adding thereto an adhesively effective quantity of an ethoxylated Bisphenol A diacrylate or dimethacrylate, whereby a storage-stable adhesive is obtained.

The adhesive is especially useful for orthodontic brackets and other orthodontic appliances that are packaged by the manufacturer with a pre-applied coating of adhesive. Shelf life characteristics such as viscosity and bond strength of the adhesive remain satisfactory for clinical use for extended periods as long as one year or greater when the adhesive is precoated on brackets and the precoated brackets are stored in certain types of sealed packages.

DETAILED DESCRIPTION OF THE PREFERRED EMBODIMENT

Figure 1:
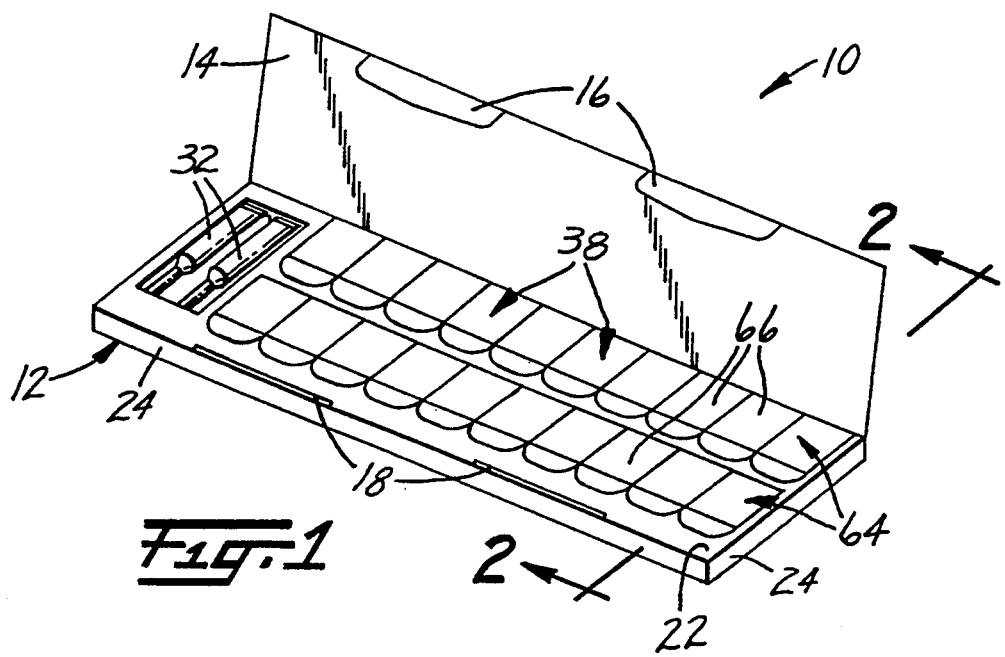
FIG. 1 is a perspective view of a dental packaging assembly useful with the adhesive of the present invention.
Figure 2:
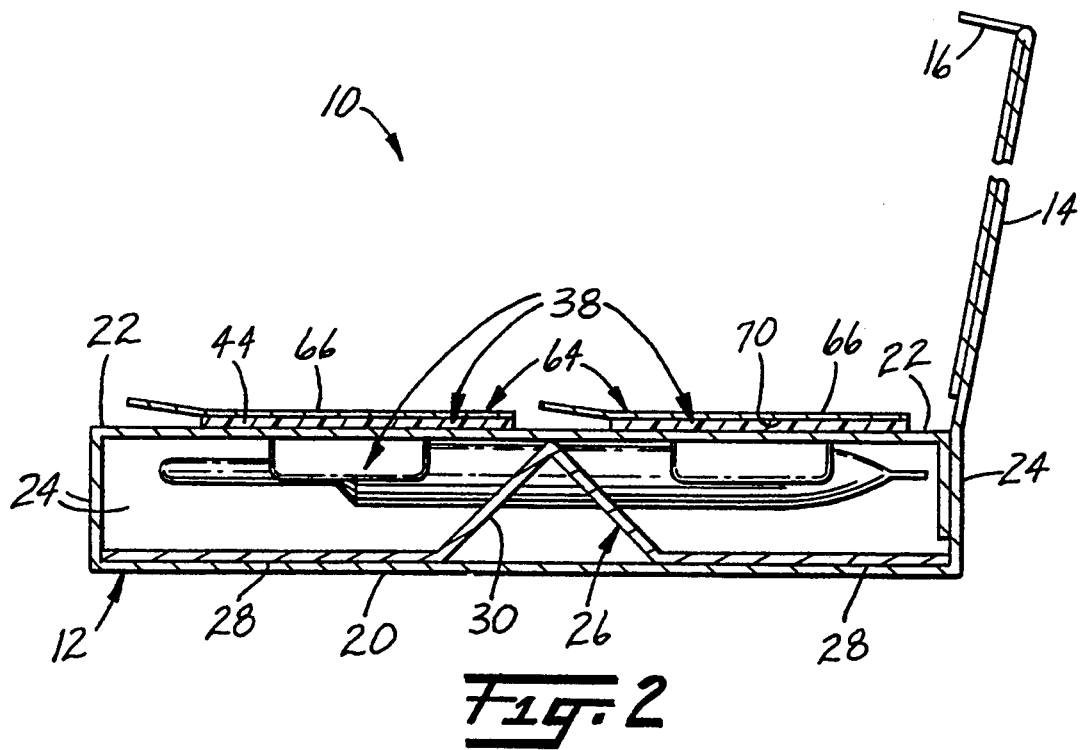
FIG. 2 is an enlarged side cross-sectional view of the assembly shown in FIG. 1.
Figure 3:
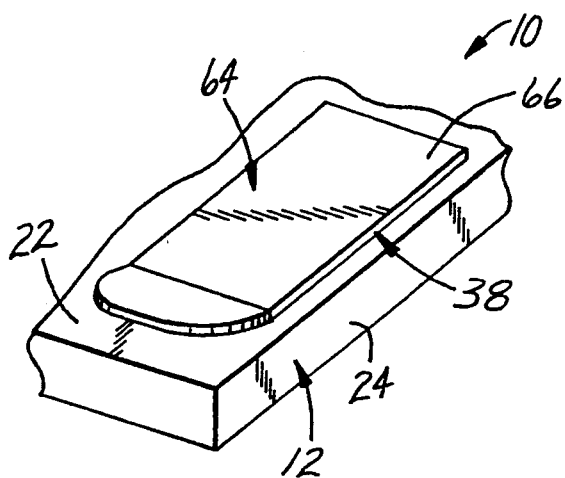
FIG. 3 is an enlarged, perspective, fragmentary view of one corner of the assembly shown in FIG. 1.
Figure 4:
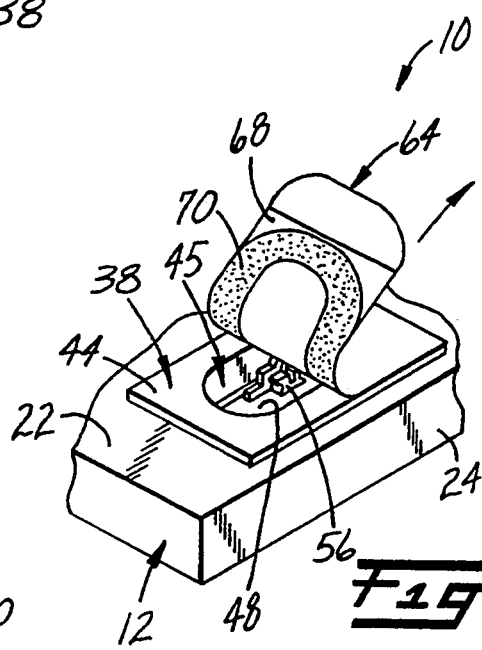
FIG. 4 is a view somewhat similar to FIG. 3 except that a cover of a container has been partially opened.

A dental packaging assembly 10 is illustrated in FIGS. 1–8, and includes a rectangular box 12 having a swingable, upper lid 14 that can be observed in FIGS. 1 and 2. A pair of tabs 16 are connected to the lid 14 and are received in respective front slots 18 (FIG. 1) in order to retain the lid 14 in a closed position when desired.

The box 12 includes a flat, rectangular bottom 20 and a flat, rectangular top carrier 22 that is interconnected with the bottom 20 by four upright walls 24. As illustrated in FIG. 2, an insert 26 is received in the chamber between the bottom 20 and the carrier 22, and the insert 26 has elongated legs 28 that rest against the walls 24. A central arch 30 of the insert 26 extends along the length of the box 12 in contact with the carrier 22 in order to support a central portion of the carrier 22. The box 12 and the insert 26 are made of 0.4 mm thick clay coated solid bleached sulfate paperboard.

A left end portion (viewing FIG. 1) of the carrier 22 has an aperture that overlies two applicator units 32 containing a swab predosed with an orthodontic adhesive primer. The units 32 are releasably received in notches formed in the arch 30 of the insert 26, and are somewhat similar to the assemblies described in U.S. Pat. No. 4,952,204, the disclosure of which is incorporated by reference herein.

The carrier 22 has edge structure 34 (FIGS. 7-8) that defines a plurality of oval-shaped openings 36 arranged in two rows. A container 38 is releasably received in each of the openings 36. Preferably, two rows of containers 38, each row containing ten containers 38, is provided to separately contain a dental appliance such as an orthodontic bracket for each tooth involved in treatment.

Each container 38 includes an upright sidewall 40 (see also FIGS. 7-8) that defines an oval in plan view. An oval-shaped bottom substrate 42 is integrally connected to the sidewall 40, and the substrate 42 and the sidewall 40 together define a well 45. The sidewall 40 is also connected to an oval-shaped central opening of a rectangular top flange 44. The sidewall 40 has two horizontally extending recesses 46 that engage the edge structure 34 of the carrier 22.

The container 38 is formed from a sheet of flexible material that provides a substantial barrier to the transmission of light. Preferably, the container 38 is black 0.33 mm thick polyethylene terephthalate glycol ("Kodar" brand PETG No. 6763, Kodak Chemical Company) that is optionally treated with a silicone release agent (No. 24, Dow Chemical). The configuration of the opening 36 presents a slight interference fit with the sidewall 40 such that the edge structure 34 will slightly deform or deflect (see FIGS. 7-8) when the container 38 is inserted in the opening 36 of the carrier 22. Normally, the deflected edge structure 34 will thereafter retain the container 38 in the opening 36, although sufficient urging of the container 38 will permit removal of the container 38 from the opening 36 when desired.

A flexible film 48 having an oval configuration in plan view is received in the well 45 as shown in FIGS. 4-8. The film 48 is a 0.05 mm thick sheet of fluorinated ethylene propylene copolymer ("Teflon" brand FEP No. 200 C, clear, E.I. du Pont de Nemours & Company) that is etched on one side by electrostatic discharge apparatus to enhance the bond to an acrylic pressure sensitive adhesive 50 (No. V-29, Flexcon Company, Inc., Spencer, Mass.) that secures the film 48 to the substrate 42 of the well 45.

Figure 7:
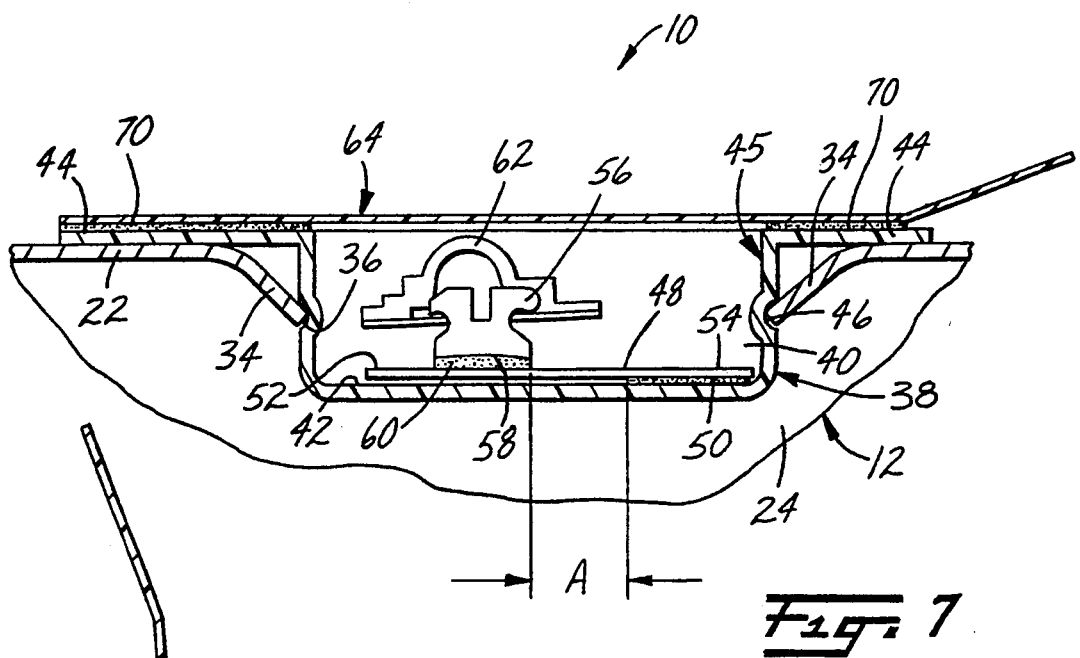
FIG. 7 is a side cross-sectional view of the container and cover shown in FIG. 3, also illustrating the bracket and flexible film in the well.
Figure 8:
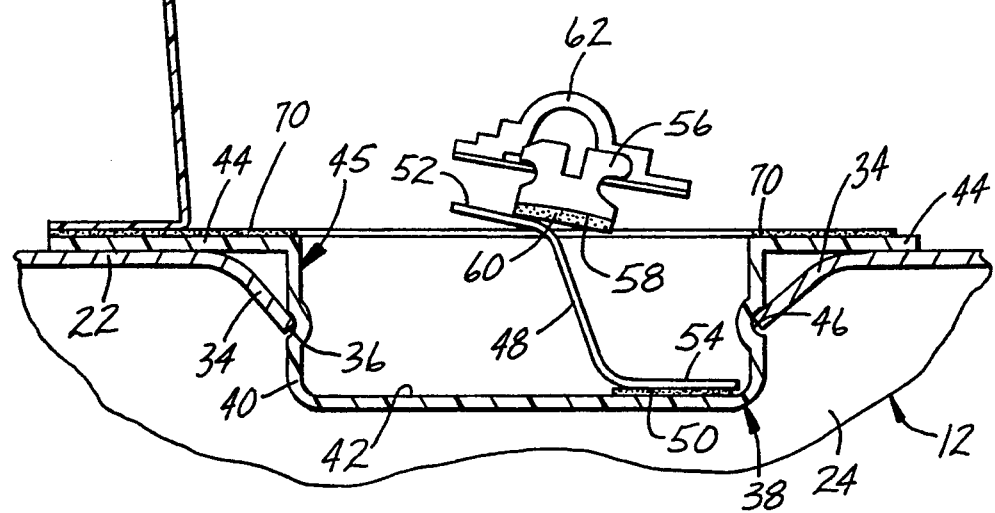
FIG. 8 is a view somewhat similar to FIG. 7 except that the cover has been opened and the bracket has been lifted from the well in similar fashion to the step shown in FIG. 5.

The film 48 has a first end section 52 that overlies a first portion of the substrate 42 on the left-hand side of the well 45 (viewing FIGS. 7-8). The pressure sensitive adhesive 50, however, only contacts a second end section 54 of the film 48 that overlies a second portion of the substrate 42 on the right-hand side of the well 45 viewing FIGS. 7-8. The second section 54 is laterally spaced from the first section 52 along the normal flat plane of the film 48 (i.e., is spaced in a horizontal direction viewing FIGS. 7-8). The first section 52 is free of pressure sensitive adhesive 50, and therefore is somewhat unrestrained and substantially free of direct connection to the substrate 42 of the well 45. The fluorinated ethylene propylene copolymer material provides a low adhesion surface for the film 48 including the surface of the first section 52 in contact with the adhesive.

An orthodontic appliance 56 is initially received in the well 45 and in the drawings comprises an orthodontic bracket made of a translucent ceramic material such as disclosed in U.S. Pat. No. 4,954,080. Alternatively, the appliance 56 could be made of other materials such as metal, glass or plastic, and could be in the form of an orthodontic buccal tube or other dental device adapted to be bonded to a tooth surface or other structure. As can be observed in FIGS. 7-8, the appliance 56 has an exterior base surface 58 having a concave, compound contour to match the contour of the tooth.

An adhesive 60 is received on the exterior surface 58 of the appliance 56 and preferably is a light-curable, non-toxic adhesive paste. Preferably the adhesive 60 is in releasable engagement with the first section 52 of the film 48 in FIGS. 4-5 and 7-8. The adhesive includes a resin system and a filler system, and the resin system includes both diglycidylmethacrylate of Bisphenol A ("Bis-GMA") and an ethoxylated Bisphenol A diacrylate ("EBDA").

EBDA includes acrylates and methacrylates. In a preferred embodiment the resin system includes Bis-GMA and ethoxylated Bisphenol A dimethacrylate ("EBDMA") along with a photoinitiator, a catalyst, an inhibitor and an amine. Sufficient EBDA is added to provide adhesively effective bond strengths for orthodontic use. Resultant bond strengths are preferably greater than about 25 kg/cm$^2$, and more preferably greater than about 54 kg/cm$^2$. While unintentional debonding of adhesives having lower bond strengths may not occur during some phases of orthodontic treatment, adhesives having higher average bond strengths are less likely to unintentionally debond during other phases of treatment that might be encountered.

Suitable EBDA viscosity-modifying components generally have a viscosity at 25° C. in the range of about 5 to 30 poise, more preferably about 6 to 25 poise and most preferably about 7 to 20 poise. Viscosity is determined by the Canon-Fenske method. Preferred commercially available EBDA components include "DIACRYL 101" (viscosity of 16 poise at 25° C.), "DIACRYL 101 W" (viscosity of 12 poise) and "DIACRYL 101 P" (viscosity of 6 poise) from Akzo Chemie America, "SR-348" and "SR-349" from Sartomer Company, Inc., "PHOTOMER 2028" and "PHOTOMER 4028" from Henkel Corporation and "EBECRYL 150" from Radcure Specialties, Inc. A particularly preferred component is EBDMA "DIACRYL 101".

The amounts of the components used in the adhesive vary depending on the desired consistency of the paste. The weight ratio of Bis-GMA/EBDMA in the resin system can range from 5/95 to 80/20 with a preferred range being from 40/60 to 70/30 and a more preferred range being from 49/51 to 63/37. The amount of photoinitiator is generally sufficient to cure the resin after a brief exposure to a curing light (e.g., 10 to 15 seconds) and is generally in the range of 0.05-0.5 weight %. The amount of catalyst is preferably about 0.2-1.0 weight %. The amount of inhibitor is preferably in the range of 0.05 to 0.2 weight % and the amount of amine is preferably about 0.2-2.0 weight %. The paste preferably comprises about 14-30 weight % resin and 86-70 weight % filler. If quartz filler is used, the paste preferably comprises about 17-22 weight % resin and about 83-78 weight % filler and more preferably about 19.5-21 weight % resin and 80.5-79 weight % filler.

The dental adhesive of the present invention can also contain suitable adjuvants such as solvents, accelerators, absorbers, diluents, stabilizers, pigments, dyes, inorganic or organic fibrous or particulate reinforcing or extending fillers, viscosity modifiers, inhibitors, surface tension depressants, wetting aids, thixotropic agents, antioxidants, medicaments (e.g., leachable fluorides), and other ingredients well known to those skilled in the art.

The viscoelastic behavior of the adhesive is determined by a consistency measurement. Consistency is measured as the spread of 1.04±0.01 g of adhesive sandwiched between two 10.16×10.16 cm glass plates under a 907.2 g weight. The adhesive is delivered onto the bottom plate, then the top plate and the 907.2 g weight are added. The combined mass of the top plate and the 907.2 g weight is 1027±10 g. After two minutes, the spread (diameter) of the adhesive is measured to the nearest 0.8 mm, and three readings are averaged. The consistency is preferably in the range of about 12 mm to 28 mm, more preferably is in the range of about 21 mm to about 26 mm, and most preferably is in the range of about 23 mm to about 24.5 mm.

A long axis indicator 62 made of poly(acrylonitrile-butadiene-styrene) (ABS) is in releasable, snap-fit contact with a side of the appliance 56 opposite the exterior surface 58. The indicator 62 serves as a guide to align the appliance 56 with the long axis of the tooth as the appliance 56 is positioned on the tooth surface. Once the adhesive 60 has cured by exposure to actinic radiation to firmly fix the appliance 56 in place on the tooth, the indicator 62 is removed from the appliance 56.

Each of the containers 38 is provided with a cover 64 to initially close the well 45. The cover 64 provides a substantial barrier to the transmission of water vapor, light and oxygen to protect the light-sensitive adhesive 60. Various suitable materials for making the cover 64 are disclosed in pending U.S. patent application Ser. No. 07/615,702, filed Nov. 20, 1990, the disclosure of which is expressly incorporated into the present disclosure.

A presently preferred assembly for making the cover 64 is shown in FIGS. 3-6 and includes a 0.025 mm clear polyester film 66 (FIG. 3) covered by a printable mat topcoat ("Compucal II" brand, No. TC-329, Flexcon), a 0.13 mm polyester intermediate film 68 having a metallized surface of aluminum bonded to the top film 66, a high tack, non-repositionable 0.018-0.02 mm thick layer of acrylic pressure sensitive adhesive (No. H529, Flexcon), followed by a 0.025 mm thick polyester carrier film and a 0.018-0.02 mm (or optionally up to 0.05 mm) thick layer of low tack, repositionable acrylic pressure sensitive adhesive 70 (FIGS. 4-6) (No. H558, Flexcon). As an alternative to the carrier film and high and low tack adhesives set out above, one side of the carrier film may be first coated with a release agent, and then both sides may be covered with a high tack pressure sensitive acrylic adhesive (No. 300, 3M Company).

The films 66, 68 extend the full length and width of the cover 64, and the non-repositionable adhesive, the carrier film and the repositionable adhesive 70 are die cut to form an oval and an adjacent endmost rectangular section. The central portion of the oval is removed and matches the shape of the well 45, such that the repositionable adhesive 70 contacts only the top flange 44 and does not extend across the well 45; rather, the well 45 when closed by the cover 64 is covered by an exposed portion of the intermediate film 68.

Figure 5:
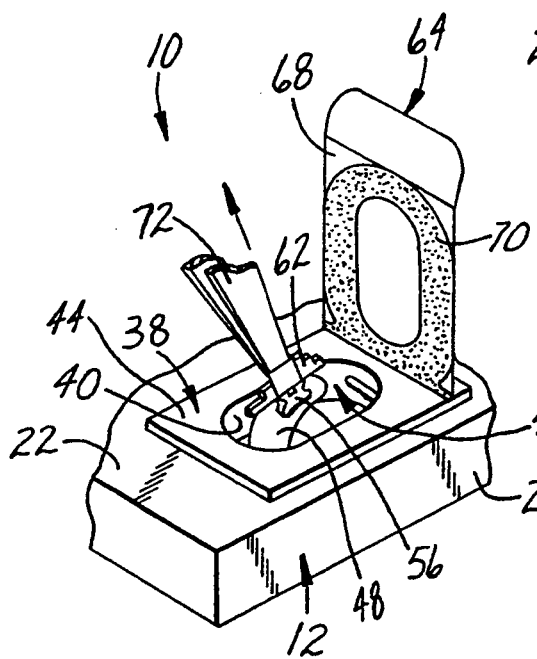
FIG. 5 is a view somewhat similar to FIG. 4 except that the cover is fully opened and a placement instrument has been inserted in a well of the container to grasp and remove an orthodontic bracket from the well.
Figure 6:
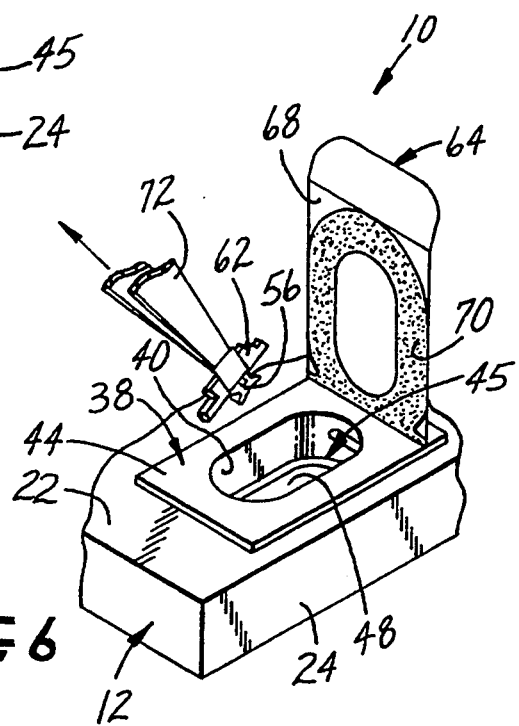
FIG. 6 is a view somewhat similar to FIG. 5 except that the bracket has been released from a flexible film secured to the well.

The cover 64 has a line of perforations 65 that defines a rear hinge portion. A front, inclined handle portion is formed for grasping the cover 64. When the handle portion of the cover 64 is grasped and pulled away from the carrier 22 in the direction of the arrow in FIG. 4, the cover 64 is moved to an open, upstanding position as shown in FIGS. 5, 6 and 8, bent at the rear line of perforations 65. The rear perforations 65 facilitate self-retention of the cover 64 in its open, upright position and permit the cover 64 to be made of relatively stiff materials. The perforations also provide tactile feedback to the user that the cover 64 is open so that the user does not continue to pull on the cover 64 and separate the latter from the carrier 22. As a result, the cover 64 along with any product identification information printed on the cover 64 is retained on the carrier 22 for future reference if needed, and the orthodontist need not dispose of a loose cover when the container 38 is opened.

The appliance 56 is firmly pressed onto the film 48 to ensure full facial contact of the adhesive 60 with the first section 52, but without force sufficient to extrude the adhesive 60 laterally from the exterior surface 58. When the cover 64 is closed, the top of the long axis indicator 62 is slightly spaced from the intermediate film 68 of the cover 64 as shown in FIG. 7. (As an alternative, the substrate 42 may have a central raised platform to decrease the space between the appliance 56 and the cover 64 when the indicator 62 is not provided).

In use, the cover 64 is opened when desired and a placement instrument 72 as shown in FIG. 5 is placed in the well 45 to grasp the sides of the appliance 56 or the sides of the indicator 62. Next, the instrument 72 is withdrawn from the well 45 in the direction of the arrows shown in FIGS. 5 and 6 until the appliance 56 with the adhesive 60 is released from the film 48. The appliance 56 is then placed on the patient's tooth, and a source of light is activated to cure the adhesive 60.

As the appliance 56 is lifted from the well 45, the first section 52 of the film 48 moves away from the substrate 42 while the second section 54 remains fixed to the substrate 42, causing the film 48 to assume a somewhat S-shaped configuration in reverse as shown in FIG. 8. Continued movement of the appliance 56 away from the substrate 42 peels the first section 52 away from the adhesive 60 such that separation between the adhesive 60 and the first section 52 substantially occurs along a line or narrow band that advances toward the left-hand side of FIG. 8. In this manner, only a relatively small area of the adhesive 60 is directly adjacent the separating surfaces at any one time. The peeling effect facilitates separation of the adhesive 60 from the film 48 while leaving the adhesive 60 substantially undisturbed and in contact with the exterior surface 58 of the appliance 56.

Preferably, the distance of separation denoted A in FIG. 7 between the appliance 56 (and the first section 52) and the pressure sensitive adhesive 50 (and the second section 54) is as large as practical so that the appliance 56 may be lifted a sufficient distance from the well 45 to facilitate peeling of the film 48 in a direction generally perpendicular to the plane of the exterior surface 58. Additionally, the second section 54 of the film 48 together with the pressure sensitive adhesive 50 are preferably located toward the front of the box 12 (i.e., next to the slots 18 and facing in a direction away from the location where the lid 14 is hinged to the box 12) to facilitate the peeling effect. The oval-shaped configuration of the film 48 lacks corners which might otherwise contact the sidewall 40 and hinder lifting of the first section 52.

The separate containers 38 in combination with the carrier 22 are advantageous during manufacture because different containers, each holding a bracket for a different tooth, can be assembled in a single kit for a particular patient in accordance with the orthodontist's prescription. Further, individual containers allow the orthodontist to open only those containers that are presently needed, so that the adhesive on the remaining brackets is not unduly exposed to light, oxygen or water vapor.

The following example is given to illustrate, but not limit, the scope of this invention. Unless otherwise indicated, all parts and percentages are by weight.

EXAMPLE

A light-curable adhesive containing 19.6% resin system and 80.4% filler system was mixed in a light-excluding mixer (Double Planetary Ross Mixer, Model LDM, Charles Ross & Son, N.Y.) and applied to orthodontic brackets. The resin system was 59.32% Bis-GMA, 38.73% EBDMA (Diacryl 101, Akzo Chemie America, distributed by Noury Chemicals, Chicago, Ill.), 0.25% camphorquinone ("CPQ", photoinitiator, Aldrich Chemical Company), 0.6% diphenyliodonium hexafluorophosphate ("$(C_6H_5)_2$ $I^+PF_6^-$", catalyst, 3M Company), 0.1% butylated hydroxytoluene ("BHT", inhibitor, Sherex Chemical Company) and 1.0% ethyl 4-dimethylaminobenzoate ("EDMAB", amine, Aldrich Chemical Company), based on the weight of the resin. The filler system used was quartz (Coleman Yards, Arkansas) comminuted to a particle surface area of 2.1–2.9 $m^2/g$ and silane-treated with 1.35% gamma-methacryloxypropyl trimethoxysilane (A-174, Union Carbide Corp.) based on the weight of the filler. The consistency of the adhesive was 23.81 mm.

Adhesive (8 mg) was syringe coated onto each base surface of 25 ceramic orthodontic brackets ("TRANSCEND 2000" brand brackets, lower anterior, Part No. 2001-721, 3M Unitek). The adhesive shear bond strength was evaluated as follows. Twenty-five bovine teeth of similar age and appearance were partially embedded in circular acrylic disks such that the enamel was exposed. The exposed surface of each tooth was polished with fine powdered Italian pumice (Servalab, Inc.) for 20 seconds, rinsed with water and air dried. The polished teeth were etched with 37% phosphoric acid etching gel for 15 seconds, rinsed with water, and air dried. An adhesive primer ("TRANSBOND" brand light cure orthodontic adhesive primer, part no. 704-059, 3M Unitek) was applied to the entire exposed enamel surface with a brush and blown into a thin film with compressed air. After each bracket was coated, the coating was pressed onto the prepared enamel surface. Residual adhesive was removed from the periphery of the bracket base and the adhesive was cured using a dental curing light ("VISILUX 2" brand, 3M Company) for 10 seconds. The bonded specimens were then stored in distilled water at 37° C. for 24 hours.

Adhesive strength was evaluated by mounting each acrylic disk in a holder clamped in the jaws of an "INSTRON" brand tensile testing apparatus with the bonded tooth surface oriented substantially in a plane parallel to the direction of pull. A loop of orthodontic wire (0.44 mm diameter) was looped under tiewings of each bracket. The ends of the orthodontic wires were clamped in the pulling jaw of the tensile testing apparatus in order to place the bond between the bracket and the tooth surface in shear stress. The crosshead speed of the tensile testing apparatus was 5 mm/min. Each bond was stressed until the bracket debonded from the tooth. The shear bond strength of twenty-five samples was averaged and for the formulation described above was $104\pm27$ $kg/cm^2$. The results show that the adhesive exhibited sufficient bond strength for clinical use.

Peel characteristics of the above adhesive when coated onto brackets were evaluated by placing 11.6 mg of adhesive onto each of 20 brackets, and 15.8 mg of adhesive onto each of 20 other brackets. The brackets were ceramic ("Transcend 2000", upper bicuspid, part no. 2001-716, 3M Unitek Corporation). A loose, oval-shaped 0.025 mm thick film of fluorinated ethylene propylene copolymer ("Teflon" brand FEP No. 200 C, white, non-etched, E.I. du Pont de Nemours & Company) was placed over the adhesive and the bracket and film were placed in containers similar to containers 38. A cover made of "Scotchmark" brand no. 7222 lidding (3M Company) was placed over each container. The lidding included 0.05 mm printable matt surface polyester, 0.025 mm high strength acrylic pressure sensitive adhesive (No. 300, 3M Company) and 0.08 mm densified white kraft paper, 55 lb (the paper was oval-shaped to match the shape of the well and covered the pressure sensitive adhesive of the lidding above the well).

After a period of at least four weeks, the covers were opened and a tweezers-like positioning instrument was used to remove each bracket from the container. The adhesive of all 40 brackets peeled away from the flexible film without substantially altering the shape of the adhesive and without leaving more than an insignificant amount of adhesive on the film.

An aging study was conducted to determine the long term stability of the adhesive. For comparison, two formulations were prepared as set out in Table 1. Sample A included triethyleneglycol dimethacrylate ("TEGDMA", Sartomer Company, Inc.) and no EBDMA, while Sample B contained EBDMA but no TEGDMA. The remaining components were identical (with the exception of the weight %) to the components of the adhesive set out above in this EXAMPLE.

TABLE 1

| COMPONENT | WEIGHT % OF ADHESIVE | |
|---|---|---|
| | SAMPLE A | SAMPLE B |
| Bis-GMA | 13.60 | 9.68 |
| TEGDMA | 4.53 | 0 |
| EBDMA | 0 | 9.68 |
| CPQ | 0.05 | 0.05 |
| $(C_6H_5)_2I^+PF_6^-$ | 0.11 | 0.12 |
| BHT | 0.02 | 0.02 |
| EDMAB | 0.18 | 0.20 |
| Filler | 81.50 | 80.25 |

100 Parts of each sample adhesive was placed in a vessel, diluted with 3.8 parts of methyl ethyl ketone ("MEK") and hand mixed with a stirring rod. Each adhesive was then immediately poured into a polypropylene syringe. The syringe plunger was immediately inserted onto the back of the syringe barrel and the knurl-lock cap attached to avoid undue loss of MEK. Ceramic orthodontic brackets ("TRANSCEND" 2000, upper bicuspid, Part no. 2001-616, 3M Unitek Corporation) were coated using a micro-fluids dispenser (Model 100, 3M Company) connected to the syringe. The coated brackets were left overnight at ambient conditions in the absence of actinic radiation to allow the MEK to evaporate and permit the adhesive to return to substantially its original viscosity.

An oval, 0.025 mm thick FEP film was placed over the adhesive coating of each bracket, and each bracket was placed in a container similar to container 38 except that the thickness of the PETG was 0.38 mm. A cover made of the "Scotchmark" brand lidding described above was placed over each container.

The packaged brackets were aged for one year and sampled at intervals ranging from weekly to monthly. Some brackets of each sample were aged at room temperature (about 22° C.), while other brackets of each sample were aged at 45° C. (Temperatures of 45° C. are sometimes encountered during shipping or storage of orthodontic products).

Prior to adhesive strength evaluation, the samples aged at 45° C. were allowed to return to room temperature. Two brackets of each sample were prepared and evaluated for adhesive shear bond strength according to the procedure described above. The brackets bonded with the formulations of Sample Nos. A and B exhibited no significant change in bond strength after one year. All samples exhibited sufficient bond strength for clinical use after aging.

At periodic intervals during the one year aging period, samples were also analyzed using gas chromatography ("GC") and high performance liquid chromatography ("HPLC") for concentration of the components in the resin system of the adhesive. For GC and HPLC testing the adhesive from fifteen brackets was combined and the components in the resin system extracted from the filler using acetonitrile. GC and HPLC results showed that after one year of room temperature aging, there was no detectable change in the concentration of either TEGDMA (Sample A) or EBDMA (Sample B). However, after aging at 45° C. for intervals longer than about 21 weeks, the concentration of TEGDMA was significantly reduced whereas the concentration of EBDMA remained substantially unchanged. After aging at 45° C. for 10 to 15 weeks, Sample A was noticeably drier and stiffer, while the flow characteristics during handling ("texture") of Sample B had not noticeably changed. Even after one year of aging, Sample B had only slightly thickened when aged at either room temperature or 45° C. and had not lost its creamy, smooth texture. Adhesives with a creamier, smoother texture are preferred by some orthodontists because such adhesives facilitate sliding the bracket on the tooth as the bracket is moved to its desired orientation, and also facilitate the step of pushing the bracket toward the tooth to firmly seat the bracket base in place.

We claim:

1. An article comprising a container with a cover, an orthodontic appliance received in said container with an adhesive on said appliance, wherein said adhesive includes an adhesively effective quantity of EBDA and is substantially free of TEGDMA so that a storage-stable adhesive is obtained, wherein the adhesive includes a resin system comprising the EBDA and a quantity of Bis-GMA, and wherein the ratio of Bis-GMA to EBDA is in the range of about 5/95 to about 80/20 by weight.

2. The article of claim 1 wherein the EBDA comprises EBDMA.

3. The article of claim 1 wherein said ratio is in the range of about 40/60 to about 70/30 by weight.

4. The article of claim 1 wherein said ratio is in the range of about 49/51 to about 63/37 by weight.

5. The article of claim 1 including a filler that comprises about 70 to about 86 weight % of said adhesive.

6. The article of claim 1 including a filler that comprises about 79 to 80.5 weight % of said adhesive.

7. The article of claim 1 including a filler comprising silane-treated quartz.

8. The article of claim 1 wherein said adhesive is light curable.

9. An article comprising a container with a cover, an orthodontic appliance received in said container and a polymerizable, storage-stable orthodontic adhesive on said appliance, said adhesive being substantially free of TEGDMA and comprising:
   (1) Bis-GMA;
   (2) a finely-divided filler; and
   (3) sufficient EBDA to impart to the adhesive (a) a consistency that will retain the orthodontic appliance in place on a vertical tooth surface during polymerization of the adhesive and (b) sufficient strength after polymerization to retain the appliance on the tooth surface during orthodontic treatment.

10. The article of claim 9, wherein said adhesive has a strength after polymerization of at least 25 kg/cm$^2$.

11. The article of claim 9, wherein said adhesive has a strength after polymerization of at least 54 kg/cm$^2$.

12. An article comprising a container with a cover, an orthodontic appliance received in said container and a polymerizable, storage-stable orthodontic adhesive on said appliance, said adhesive being substantially free of TEGDMA, having a consistency of at least about 12 mm and comprising Bis-GMA, a finely-divided filler, and EBDA.

13. The article of claim 12 wherein said consistency is in the range of about 21 mm to about 26 mm.

14. The article of claim 12 wherein said EBDA comprises EBDMA.

15. The article of claim 14 wherein said consistency is in the range of about 23 mm to 24.5 mm.

16. The article of claim 12 wherein said EBDA has a viscosity in the range of about 6 to 25 poise.

17. The article of claim 12 wherein said EBDA has a viscosity in the range of about 7 to 20 poise.

18. The article of claim 12 wherein said consistency is in the range of about 23 mm to 24.5 mm.

* * * * *